United States Patent [19]

Sturm et al.

[11] 4,072,721
[45] Feb. 7, 1978

[54] PURIFICATION OF HYDROQUINONE

[75] Inventors: Budd Harvey Sturm, Hartville; Thomas James Slam, Parma, both of Ohio

[73] Assignee: The Goodyear Tire & Rubber Company, Akron, Ohio

[21] Appl. No.: 604,273

[22] Filed: Aug. 13, 1975

[51] Int. Cl.² .............................................. C07C 39/08
[52] U.S. Cl. ............................ 260/621 A; 260/621 H
[58] Field of Search ............... 260/621 A, 627 R, 625, 260/621 H

[56] References Cited

U.S. PATENT DOCUMENTS

| | | | |
|---|---|---|---|
| 3,437,699 | 4/1969 | Flickinger | 260/621 A |
| 3,884,983 | 5/1975 | Burkholder | 260/621 A |
| 3,895,079 | 7/1975 | Anderson et al. | 260/621 A |

Primary Examiner—James O. Thomas, Jr.
Assistant Examiner—W. B. Lone
Attorney, Agent, or Firm—F. W. Brunner; J. Y. Clowney

[57] ABSTRACT

There is disclosed the method of preparing photographic grade hydroquinone from technical grade hydroquinone which consists of treating a solution of the technical grade hydroquinone in the presence of a palladium catalyst with hydrogen while the hydroquinone solution is at a pH between about 3 and about 6.

7 Claims, No Drawings

PURIFICATION OF HYDROQUINONE

This invention is directed to the treatment of technical grade hydroquinone to produce photographic grade hydroquinone. More specifically, it is directed to a new and improved process whereby technical grade hydroquinone is treated with hydrogen in the presence of palladium catalyst to produce photographic grade hydroquinone.

Commercially available technical grade hydroquinone has a relatively high platinum/cobalt color number and is not suitable for use in photographic purposes. This relatively high platinum/cobalt number in technical grade hydroquinone results from the presence of certain impurities which impart a tan to yellow to even brown color in technical grade hydroquinone.

As employed in this application, the term "technical grade hydroquinone" is meant to relate that the hydroquinone exhibits a platinum/cobalt (pt/co) color number of 45 or even higher and in some cases up to and above 500. The term "photographic grade hydroquinone" is meant that the hydroquinone exhibits a pt/co color number around 20 or slightly higher and up to about 30.

The platinum/cobalt (pt/co) color number as employed in this application is a well-known test, in which most often color is determined by visual comparisons of a test sample of hydroquinone solution against a solution with known concentrations of color solutions on the pt/co scale. The unit of color is defined as that color product produced by one milligram/per liter of platinum in the form of the chloroplatinate ion. The accuracy of such a visual test is dependent to a large extent on the judgment of the beholder. To eliminate this error, a spectrophotometry test has been devised. The spectrophotometry test was devised in the following manner.

In the standard pt/co color test, 1.246 grams of potassium chloroplatinate and 1.0 gram of cobaltous chloride are dissolved in about 100 ml of water and 100 ml of hydrochloric acid and then the solution is diluted with more water to 1-liter. To prepare the color standards, dispense varying amounts of this color stock into 100 ml volumetric flasks and dilute to 100 ml with water, for example:

| pt/co color | ml of stock diluted to 100 ml |
| --- | --- |
| 5 | 1 |
| 10 | 2 |
| 15 | 3 |
| 20 | 4 |
| 25 | 5 |
| 30 | 6 |
| 35 | 7 |
| 40 | 8 |
| 45 | 9 |
| 50 | 10 |

The relationship of the above table goes on up in a similar fashion to higher pt/co color numbers. Measure the absorbance of each standard solution at 390 m$\mu$, record the absorbance and its pt/co number and prepare a calibration curve of the absorbance at 390 m$\mu$ versus the pt/co number.

To obtain the pt/co color number of any given sample of hydroquinone, weigh 5.0 grams into a 100 ml volumetric flask, add 80 ml of dilute acetic acid and shake to dissolve, make up to 100 ml with dilute acetic acid and measure absorbance at 390 m$\mu$ versus a reference of dilute acetic acid. Using the calibration curve, obtain the pt/co color number of the test sample of hydroquinone. It has been found that at 390 millimicrons (m$\mu$), the absorbance of hydroquinone is a straight line relationship with the pt/co color number, thus the slope of the curve could be used to calculate the pt/co color number.

Certain processes are known whereby technical grade hydroquinone is upgraded to photographic grade. One consists of treating the technical grade hydroquinone while in solution with activated carbon to adsorb the impurities from the solution of hydroquinone, but this process uses rather large amounts of activated carbon. Another method employed is to reduce technical grade hydroquinone with inorganic reducing agents, however this process leaves residues of the inorganic reducing agents in the resulting hydroquinone which in themselves are impurities. For these reasons, these processes leave something to be desired.

It has now been found in accordance with this invention that a slightly acid solution of technical grade hydroquinone can be treating with hydrogen in the presence of palladium catalyst to produce photographic grade hydroquinone.

A more detailed description of the invention is that technical grade hydroquinone is put into solution using any solvent. The pH of the technical grade hydroquinone solution should be adjusted between about 3 and about 6 for best results. If the pH of the solution of the technical grade hydroquinone is neutral, basic or has a pH much below 3, the process yields dark crystalline hydroquinone unsuited for photographic grade. Any solvent system in which hydroquinone is soluble could be employed, so long as the solvent does not adversely affect the catalyst activity or the hydroquinone. However, water is ideal as a solvent because of the ease of adjusting the pH to the proper level and the ease of recovery of the reduced or photographic grade hydroquinone.

As has been indicated, the invention is the reduction of the impurities in technical grade hydroquinone while said hydroquinone is in a solution adjusted so that the pH ranges from about 3.0 to about 6.0. This reduction takes place in the presence of a palladium catalyst and hydrogen is used as a reducing agent.

The actual operating conditions other than those mentioned in the previous paragraph are not critical to the actual invention. For instance, the temperature, the pressure of hydrogen, the residence times and even the amount of catalyst are all interdependent on each other, the kind and amount of impurities present in the technical grade hydroquinone as well as the purity desired of the photographic grade. These operating conditions also depend on other factors, such as, the dilution or concentration of the hydroquinone, the proper contact between the impurities and the hydrogen and the catalyst and other factors which those skilled in the art will readily be able to determine without undue experimentation.

It has been found, however, that the reduction of the technical grade hydroquinone impurities or color bodies can be successfully carried out at temperatures ranging between about 25° and about 25° C, with about 50° to about 80° C being more preferred. It has been observed that if the solution of hydroquinone in its solvent is at too high a temperature there may be a tendency to cause a reduction of the aromatic ring of the hydroquinone. On the other hand, care must be taken that too low a temperature is not used so that some of the hydroquinone will not fully be dissolved in the solvent employed and therefore its impurities will not be in contact with either the hydrogen of the catalyst.

The concentration of the hydroquinone in its solvent has not been found to be at all critical. It must be appreciated however that a sufficient amount of solvent be employed so that the hydroquinone is soluble at the operating temperatures chosen.

The pressure of the hydrogen employed in this invention has not been found critical and can vary from atmospheric pressure to several hundred atmospheres with about 5 to about 150 psig being more preferred.

The amount of hydrogen required in the reduction of the impurities in the practice of this invention depends, of course, on the quantity and type of impurities in the technical grade and the purity of the photographic grade desired as well as the contact of the hydroquinone with the catalyst. Also, the time required would have some bearing on the amount of hydrogen to be employed. As indicated, good results have been obtained using hydrogen pressure varying between about 5 and about 150 psig.

The time referred to as contact time required for the reduction of the impurities like some of the other operating conditions depends on various other factors such as, the type and amount of impurities, the hydrogen pressure, the temperature and amount and type of impurities also the purity desired in the final product. Times varying between ten seconds and two hours have been satisfactorily employed with thirty seconds to ten minutes being preferred.

It should be pointed out that the temperature, the pressure and the time all will have a bearing on the economics of the process. If the pressures are extremely high, the temperature extremely high and the times extremely long, there is a likelihood of the reduction of the aromatic ring of the hydroquinone. On the other hand, if these variables are too low or too short, the reduction may not be sufficient to remove the color bodies or impurities and photographic grade may not be obtained.

Those skilled in the art will readily adjust the various operated parameters to give the best and most economical results.

The catalyst employed in this invention is palladium. In order to effect economies, it is preferred that the palladium be supported on any inert support which would not adversely affect the reaction. Any of the more common supports which are inert in a hydrogenation reaction can be employed. It has been found that palladium on alumina and palladium on carbon works very well. If the palladium is employed on a support, the catalyst loading on the support can vary rather widely from about 0.001 to about 10 percent by weight. It has been found that catalyst loadings of much below 0.1 and much above 1.0 have certain minor deficiencies. If the loading is much below 0.1 percent, the product produced still had some color indicating an incomplete reduction of the impurities. On the other hand, if the catalyst loading exceeds much above 1 percent, there is a danger of excessive reduction of the aromatic ring of the hydroquinone and the expense of unneeded catalyst.

The process herein described may be carried out either batch-wise or as a continuous process. The process is, as indicated, carried out in solution. The process is preferably carried out in the absence of oxygen as oxygen will tend to oxidize hydroquinone as well as the impurities when it is in solution. Furthermore, the palladium catalyst employed in the process in addition to being a reducing catalyst is an excellent oxidative catalyst. The oxidation products of hydroquinone lend color to the final product, thus it is preferable that air or oxygen be excluded from the process.

The product hydroquinone after being reduced with hydrogen over the palladium catalyst is cooled to a temperature whereby the hydroquinone crystallizes and is usually filtered or centrifuged to remove excess solvent and the hydroquinone dried. Any hydroquinone which remains in solution during the filtering or centrifuging step can be recycled to the process for further reduction and/or recovery.

The invention is further illustrated by reference to the following examples which are intended to be illustrative rather than limiting of the scope of the invention.

EXAMPLE I

Into a 1-liter stainless stell autoclave equipped with a turbine stirrer, baffles, thermocouple wells, electric heaters and a temperature controller was charged 100 grams technical grade hydroquinone, 1 gram of powdered catalyst composed of 0.5 percent by weight of palladium on carbon, 400 milliliters of distilled water. The autoclave was closed and hydrogen gas was introduced to a pressure of 60 psig. The reaction mixture was stirred with the stirrer and the mixture was heated to 60° C and held at that temperature for 1.5 hours. At the end of that time, the stirrer was stopped and the excess hydrogen was vented from the autoclave and the reduced hydroquinone was withdrawn from the autoclave. The solution was immediately filtered to remove it from the catalyst and then 10 grams of activated charcoal was added to the mixture and was stirred at 80° under an atmosphere of nitrogen. The activated charcoal was separated by filtration and the solution was cooled to 15° C with no agitation under an atmosphere of nitrogen. White crystalline hydroquinone was filtered off and dried in a vacuum oven at 60° C for approximately 15 hours. About 60 grams of hydroquinone having a pt/co color number of 19 was obtained. The original technical grade hydroquinone had a pt/co number above 500. The total hydroquinone balance was 98 percent.

EXAMPLE II

In an autoclave like that of Example I was charged 100 grams technical grade hydroquinone, 5 grams of powdered catalyst composed of 0.5 percent by weight of palladium on carbon, 400 milliliters of distilled water. The autoclave was closed and pressured with hydrogen to 60 psig. The mixture was stirred and heated to 60° C and maintained for 1.5 hours. The reduced hydroquinone was recovered in the same manner as in Example I. The pt/co color of the original hydroquinone was 44, the color after hydrogenation was 21 and after being treated with the activated charcoal, the color was 14. The total hydroquinone balance was 100 percent.

The technical grade hydroquinone to which the process of this invention is particularly adaptable to be used to prepare photographic grade hydroquinone are the two commercial processes for the preparation of technical grade hydroquinone known to the applicants.

It is known that hydroquinone may be prepared from aniline by oxidizing aniline with manganese dioxide in the presence of excess sulfuric acid to form quinone and as a by-product manganese sulfate and ammonium sulfate. This quinone is then neutralized with lime or some other base and steam distilled from the mixture. The purified quinone is reduced to hydroquinone using an iron powder or even hydrogen.

The other known commercial process for the production of technical grade hydroquinone is one where benzene or cumeme is alkylated with propylene to form diisopropylbenzene which is then oxidized with oxygen to form diisopropylbenzenehydroperoxide. The diisopropylbenzenehydroperoxide is rearranged in the presence of sulfuric acid to form hydroquinone and acetone.

These two known commercial methods for the preparation of hydroquinone can be schematically represented as follows:

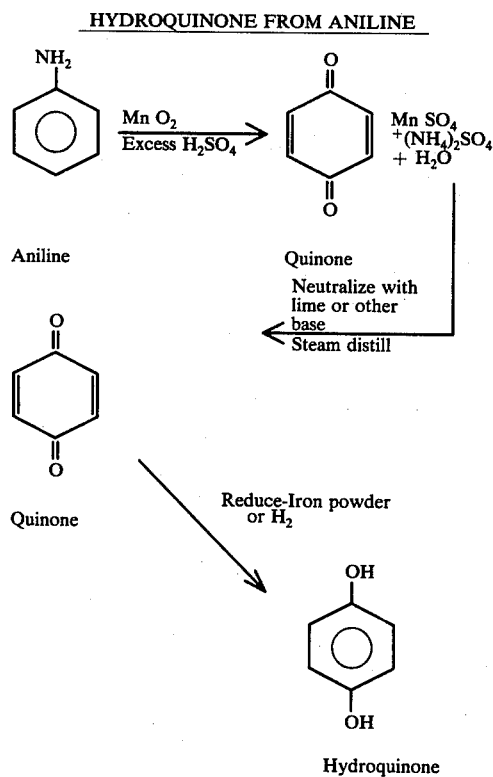

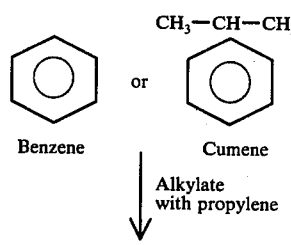

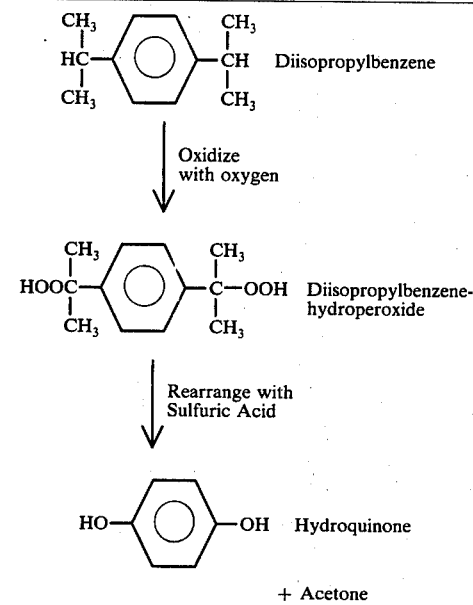

+ Acetone

The technical grade hydroquinone converted into photographic grade hydroquinone in Example I was hydroquinone prepared from benzene or cumene. The technical grade hydroquinone coverted into photographic grade hydroquinone in Example II was hydroquinone prepared from aniline.

While certain representative embodiments and details have been shown for the purpose of illustrating the invention, it will be apparent to those having skill in this art that various modifications and changes may be made therein without departing from the spirit or scope of the invention.

What is claimed is:

1. In the method of subjecting technical grade hydroquinone to a process which consists of preparing a water solution of technical grade hydroquinone and subsequently treating such water solution with hydrogen at pressures from about 5 to about 150 psig while in the presence of from about 0.1 to about 1 percent by weight of palladium on a support, at temperatures ranging from about 25 to about 125° C. and recovering photographic hydroquinone from said solution which improvement comprising adjusting the pH of the water solution of hydroquinone to a pH between about 3 and about 6.

2. The method of claim 1 in which the support is alumina or carbon.

3. The method according to claim 1 in which the technical grade hydroquinone is in a water solution.

4. The method according to claim 1 in which the contact time varies from about 10 seconds to about 2 hours.

5. The method according to claim 4 in which the contact time varies from about 30 seconds to about ten minutes.

6. The method according to claim 1 in which the palladium is employed on an inert support.

7. The method according to claim 1 wherein the technical grade hydroquinone is treated with hydrogen in the presence of a palladium catalyst in which the temperature varies from about 50 to about 80° C, the hydrogen pressure varies from about 5 to about 150 psig, and in which the contact time varies from about 30 seconds to about two hours and in which the palladium varies from about 0.1 to about 1 percent by weight on a support which is alumina or carbon.

* * * * *